US008372421B2

(12) United States Patent
Galloway et al.

(10) Patent No.: US 8,372,421 B2
(45) Date of Patent: Feb. 12, 2013

(54) INHIBITION OF MITOGEN-ACTIVATED PROTEIN KINASES IN CARDIOVASCULAR DISEASE

(75) Inventors: Aubrey Galloway, Bronxville, NY (US); Paolo Mignatti, New York, NY (US); Giuseppe Pintucci, Tuckahoe, NY (US)

(73) Assignee: New York University, New York, NY (US)

( * ) Notice: Subject to any disclaimer, the term of this patent is extended or adjusted under 35 U.S.C. 154(b) by 349 days.

(21) Appl. No.: 12/624,362

(22) Filed: Nov. 23, 2009

(65) Prior Publication Data

US 2010/0069503 A1  Mar. 18, 2010

Related U.S. Application Data

(63) Continuation of application No. 11/207,613, filed on Aug. 19, 2005, now abandoned.

(60) Provisional application No. 60/603,493, filed on Aug. 20, 2004.

(51) Int. Cl.
*A61F 2/00* (2006.01)

(52) U.S. Cl. ...... 424/423; 424/426; 623/1.11; 623/1.43; 623/1.46; 435/184

(58) Field of Classification Search ........................ None
See application file for complete search history.

(56) References Cited

U.S. PATENT DOCUMENTS

| 5,820,583 | A | 10/1998 | Demopulos et al. |
| 7,244,441 | B2 | 7/2007 | Schreiner |
| 2003/0044412 | A1 | 3/2003 | Pietras et al. |
| 2003/0060877 | A1 | 3/2003 | Falotico et al. |
| 2003/0170287 | A1 | 9/2003 | Prescott |
| 2003/0176437 | A1 | 9/2003 | Watterson et al. |

FOREIGN PATENT DOCUMENTS

| WO | 9300051 A1 | 1/1993 |
| WO | 9300052 A1 | 1/1993 |
| WO | 2005030091 A2 | 4/2005 |

OTHER PUBLICATIONS

Alt E. et al., Inhibition of Neointima Formation After Experimental Coronary Artery Stenting: A New Biodegradable Stent Coating Releasing Hirudin and the Prostacyclin Analogue Iloprost, Circulation, Mar. 28, 2000, vol. 101, pp. 1453-1458.*
Indolfi C. et al., Molecular Mechanisms of In-Stent Restenosis and Approach to Therapy with Eluting Stents, Trends Cardiovasc. Med., 2003, vol. 13, No. 4, pp. 142-148.*
Gulkarov, Iosif et al., "Topical Mitogen-Activated Protein Kinases Inhibition Reduces Intimal Hyperplasia in Arterialized Vein Grafts", Journal of Surgical Research, vol. 154, pp. 150-156, 2009.
Burton E. Sobel, Coronary Artery Disease, Current Science, vol. 3, No. 3, Mar. 1992.
Pintucci, et al., 1999. Mechanical endothelial damage results in basic fibroblast growth factor—mediated activation of extracellular signal-regulated kinases, Surgery, vol. 126, No. 2, pp. 422-427.
Pintucci, et al., Lack of ERK activation and cell migration in FGF-2-deficient endothelial cells, The FASEB Journal express article 10.1096/fj.01-0815fje. Published online Feb. 25, 2002.
Pintucci et al., Lack of ERK activation and cell migration in FGF-2-defiicient endothelial cells, The FASEB Journal, vol. 16, Apr. 2002.
Schwartz, et al., 1988. Aspirin and Dipyridamole in the Prevention of Restenosis after Percutaneous Transluminal Coronary Angioplasty, The New England Journal of Medicine, vol. 318, No. 26:1714-1719.
Wolinsky, et al., Use of a Perforated Balloon Catheter to Deliver Concentrated Heparin into the Wall of the Normal Canine Artery, JACC vol. 15, No. 2, Feb. 1990:475-81.
Jorgensen et al., Femoral Artery Recanalisation with Percutaneous Angioplasty and Segmentally Enclosed Plasminogen Activator, The Lancet, May 20, 1989, 1106-1108.
Dichek, Interventional Approaches to the Introduction of Genetic Material into the Vasculature, VI Gene Transfer and Therapy, 989-1005. In: Topol EJ, ed. Textbook of Interventional Cardiology. Philadelphia, Pa: WB Saunders; 1994.
Casey, et al., 2001. Gene Targeting via Triple-Helix Formation, Progress in Nucleic Acid Research and Molecular Biology, vol. 67:163-193.
Meier, Prevention of restenosis after coronary angioplasty: A pharmacological approach, European Heart Journal, 1989, 10, Supplement G, 64-68.
Pintucci, et al., Induction of Stromelysin-1 (MMP-3) by Fibroblast Growth Factor-2 (FGF-2) in FGF-2 Microvascular Endothelial Cells Requires Prolonged Activation of Extracellular Signal-Regulated Kinases-1 and -2 (ERK-1/2), Journal of Cellular Biochemistry 90:1015-1025 (2003).
Cech, et al., Biological Catalysis by RNA, Ann. Rev. Biochem. 1986, 55:599-629.
Barner, et al., Twelve-year experience with internal mammary artery for coronary artery bypass, J Thorac Cardiovasc Surg 90-668-675, 1985.
Bosher, et al., RNA interference: genetic wand and genetic watchdog, Nature Cell Biology, vol. 2, Feb. 2000, E31-E36.
Sharp, et al., Molecular Biology: RNA Interference, Science, vol. 287, Issue 5462, 2431-2433, Mar. 31, 2000.
Blake, et al., C-Reactive Protein and Other Inflammatory Risk Markers in Acute Coronary Syndromes, Journal of the American College of Cardiology, vol. 41, No. 4, Suppl. S, Feb. 19, 2003:37S-42S.
Yeh, et al., Coming of Age of C-Reactive Protein Using Inflammation Markers in Cardiology, Circulation, Jan. 28, 2003, 370:372.
Nielsen, et al., Sequence-Selective Recognition of DNA by Strand Displacement with a Thymine-Substituted Polyamide, Science, vol. 254, 1497:1500, (1991).
Koyama, et al., Cell Replication in the Arterial Wall Activation of Signaling Pathway Following in Vivo Injury, Circulation Research, 713:721, (1998).
Research Letters, The Lancet, vol. 364, Oct. 23, 2004, 1466:1521.

(Continued)

*Primary Examiner* — Jon P Weber
*Assistant Examiner* — Satyendra Singh
(74) *Attorney, Agent, or Firm* — Fish & Richardson P.C.

(57) ABSTRACT

The present invention relates to methods for inhibiting subacute thrombosis and/or intimal hyperplasia following an interventional vascular procedure by contacting a blood vessel or a synthetic material with a mitogen-activated protein kinase (MAPK) pathway inhibitor. The present invention further relates to vascular devices comprising a MAPK pathway inhibitor.

2 Claims, 4 Drawing Sheets

OTHER PUBLICATIONS

Ragosta, et al., Specific Factor Xa Inhibition Reduces Restenosis after Balloon Angioplasty of Atherosclerotic Femoral Arteries in Rabbits, Circulation, vol. 89, No. 3, Mar. 1994, 1262:1271.

Bizekis, et al., Activation of mitogen-activated protein kinases during preparation of vein grafts and modulation by a synthetic inhibitor, The Journal of Thoracic and Cardiovascular Surgery, vol. 126, No. 3, 659:665, (2003).

Milella, et al., Therapeutic targeting of the MEK/MAPK signal transduction module in acute myeloid leukemia, The Journal of Clinical Investigation, Sep. 2001, vol. 108, No. 6, 851:859.

Bogoyevitch, Signalling via stress-activated mitogen-activated protein kinases in the cardiovascular system, Cardiovascular Research, 45 (2000) 826-842.

Saunders, et al., Vein graft arterialization causes differential activation of mitogen-acivated protein kinases, The Journal of Thoracic and Crdiovascular Surgery, May 2004, 1276:1284.

Li, et al., Biphasic pro-thrombotic and inflammatory responses after coronary artery bypass surgery, Journal of Thrombosis and Haemostasis, 1:470-476, (2002).

Davis, et al., The role of inflammation in vascular injury and repair, Journal of Thrombosis and Haemostasis, 1:1699:1709, (2003).

Banfi, C. et al., "Induction of Plasminogen Activator Inhibitor I by the PPARa Ligand, Wy-14,643, Is Dependent on EKR 1/2 Signaling Pathway", Thromb Haemost, 2003, pp. 611-619, vol. 90.

Woods, D. et al., "Induction of b3-Integrin Gene Expression by Sustained Activation of the Ras-Regulated Raf-MEK-Extracellular Signal-Related Kinase Signaling Pathway", Molecular & Cellullar Biology, May 2001, pp. 3192-3205, vol. 21, No. 9.

DeWitt, D.L., 1999. "Cox-2-selective inhibitors: the new super aspirins, a minireview." Molecular Pharmacology 55: 625-631.

Newton, et al, 2000. "The MAP kinase inhibitors, PD98059, UO126, and SB203580, inhibit IL-1beta-dependent PGE2 release via mechanistically distinct processes." British Journal of Pharmacology 130(6): 1353-1361.

Bavry et al., Late Thrombosis of Drug-Eluting Stents: A Meta-Analysis of Randomized Clinical Trials, Am. J. Med., vol. 119, pp. 1056-1061, 2006.

Indolfi et al., In vivo gene transfer: prevention of neointima formation by inhibition of mitogen-activated protein kinase kinase, Basic Res. Cardiol., vol. 92, pp. 378-384, 1997.

Infolfi et al Inhibition of cellular *ras* prevents smooth muscle cell proliferation after vascular injury in vivo, Nature Medicine, vol. 1, pp. 541-545, 1995.

Jackson et al., Pharmacotherapy to improve outcomes in vascular access surgery: a review of current treatment strategies, Nephrol. Dial. Transplant., vol. 27, pp. 2005-2016, 2012.

Johnson et al., The role of MKK1/2 kinase activity in human cytomegalovirus infection, J. Gen. Virol., vol. 82, pp. 493-497, 2001.

McFadden et al., Late thrombosis in drug-eluting coronary stents after discontinuation of antiplatelet therapy, Lancet, vol. 364, pp. 1519-1521, 2004.

Muto et al., Mechanisms of Vein Graft Adaptation to the Arterial Circulation—Insights Into the Neointimal Algorithm and Management Strategies, Circulation J., vol. 74, pp. 1501-1512, 2010.

Pintucci et al., Anti-proliferative and anti-inflammatory effects of topical MAPK inhibition in arterialized vein grafts, FASEB J., vol. 20, pp. 398-400, 2006.

London and Clayton, Functional identification of sensory mechanisms required for developmental song learning, Nature Neuroscience, vol. 11, pp. 579-586, 2008.

Gennaro et al , Inhibition of Vascular Smooth Muscle Cell Proliferation and Neointimal Formation in Injured Arteries by a Novel, Oral Mitogen-Activated Protein Kinase/Extracellular Signal-Regulated Kinase Inhibitor, Circulation, vol. 110, pp. 3367-3371, 2004.

Favata et al., Identification of a Novel Inhibitor of Mitogen-activated Protein Kinase Kinase, J. Biol. Chem., vol. 273, pp. 18623-18632, 1998.

Eisenberg, Drug-eluting stents: some bare facts, Lancet, vol. 364, pp. 1466-1467, 2004.

Duncia et al., MEK Inhibitors: the Chemistry and Biological Activity of U0126, its Analogs, and Cyclizatoin Products, Bioorg. Med. Chem. Lett., vol. 8, pp. 2839-2844, 1998.

\* cited by examiner

INHIBITION OF MITOGEN-ACTIVATED PROTEIN KINASES IN CARDIOVASCULAR DISEASE

CROSS REFERENCE TO RELATED APPLICATIONS

The present application is a Continuation of U.S. patent application Ser. No. 11/207,613, filed Aug. 19, 2005, which claims the priority to U.S. Provisional Patent Application Ser. No. 60/603,493, filed Aug. 20, 2004, both of which are hereby incorporated by reference in their entireties.

FIELD OF THE INVENTION

The present invention relates to methods for inhibiting subacute thrombosis, intimal hyperplasia, or both following an interventional vascular procedure by contacting a blood vessel or a synthetic material with a mitogen-activated protein kinase (MAPK) pathway inhibitor. The present invention further relates to vascular devices comprising a MAPK pathway inhibitor.

BACKGROUND

Atherosclerosis results from vascular injury induced by multiple insults including hypercholesterolemia, diabetes, smoking, and hypertension. Atherosclerosis is responsible for approximately 50% of all deaths in the developed world (Davis et al., J Thromb Haemostas. 2003; 1:1699-1709). Depending on the degree of narrowing and the specific vessel(s) involved, atherosclerosis can lead to pathologic conditions throughout the body, including: coronary artery disease, cerebrovascular disease, peripheral vascular disease, and renovascular disease.

Interventional treatments for atherosclerotic lesions include percutaneous procedures, such as balloon angioplasty with or without stenting, and surgical procedures, such as vascular bypass of a stenotic lesion. Coronary artery bypass grafting (CABG) utilizes arteries (e.g., the left internal mammary artery) and/or veins (e.g., the saphenous vein) as the bypass conduit. Non-cardiac bypass procedures, e.g., femoral-popliteal artery bypass, also utilize synthetic conduits.

Vascular interventions such as atherectomy, angioplasty with or without stent placement and vascular bypass are accompanied by vascular injury to the vessel being intervened upon, nearby blood vessels, and/or, in the case of autologous conduit grafting, in the vascular conduit. This injury can lead to early (subacute) thrombosis (SAT) or, later, intimal hyperplasia. Subacute thrombosis and intimal hyperplasia are significant concerns following angioplasty and stent placement, and can lead to restenosis (U.S. Pat. No. 6,723,120). Stenotic lesions that have been dilated by angioplasty restenose in up to 50% of cases (U.S. Pat. No. 6,730,313). Following CABG, the 5 and 10-year patency rates of saphenous vein grafts are approximately 74% and 41%, respectively (Barner et al., J Thorac Cardiovasc Surg. 1985; 90:668-75). Depending on the location of the affected vessel, restenosis can result in myocardial infarction, stroke or limb loss.

Damage to the vascular endothelium compromises the balance between antithrombotic and prothrombotic factors and results in thrombus formation (Davis, et. al.). The endothelium plays key roles in the vascular response to injury, including the regulation of leukocyte adhesion, platelet aggregation and adhesion, and hemostasis/thrombosis. In performing these functions, the endothelium expresses and responds to cytokines, chemokines, and cell adhesion molecules. Vessel injury results in endothelial damage that compromises the endothelium's normal physiological role and triggers an inflammatory response including platelet activation, leukocyte infiltration into the vessel wall, smooth muscle cell proliferation and migration, and extracellular matrix deposition (Davis et al.).

Early graft failure is related to thrombosis and inflammation. A clinical study of patients after cardiac surgery showed that CABG induces marked pro-thrombotic and inflammatory responses, which persist for at least one week (Li, et al., J Thromb Haemostas. 2003; 1(3):470(abstract)). Vascular injury also triggers a remodeling process characterized by the loss of the inner cellular coating of the vessel (intima) and induction of proliferation and migration of smooth muscle cells from the middle layer of the vessel wall (media). These smooth muscle cells migrating into the intima form a "neointima." The growth of the neointima and deposition of extracellular matrix ultimately results in an abnormally thick inner layer (intimal hyperplasia) and consequent narrowing of the vessel lumen (restenosis). Thus, vessel injury can result in subacute thrombosis or intimal hyperplasia, or both.

Mitogen-activated protein kinases (MAPK) have been identified as key intracellular signaling mediators responsible for the cellular proliferation, migration, and apoptosis involved in vascular remodeling (Bogoyevitch M A, Cardiovasc Res. 2000; 45:826-42). Three major MAPK pathways have been characterized: extracellular signal-regulated kinases (ERKs), stress-activated protein kinases (JNKs), and stress-activated $p38^{MARK}$. The ERK pathway is predominately activated following the interaction of growth factors with their specific cell tyrosine kinase receptors. JNK and $p38^{MAPK}$ are highly responsive to stress stimuli (Bizekis, et al., J Thorac Cardiovasc Surg. 2003; 126:659-65). MAPKs are activated upstream in the MAPK pathway by kinases (MAPK kinases) known as MEKs (Milella et al., J Clin Invest. 2001; 108(6):851-859). Studies on cultured endothelial and smooth muscle cells or on in vivo injured arteries have linked MAPK activation to cell proliferation, migration, and apoptosis. Saphenous vein excision and preparation for grafting result in activation of ERKs and JNKs. Id.

The synthetic MAPK pathway inhibitor PD98059, an inhibitor of the ERK-1/2 pathway at the MEK-1/2 level, has been shown to inhibit ERK activation and medial cell proliferation when delivered pre- and post-operatively to rats with balloon-injured carotid arteries (Koyama et al., Circ Res. 1998; 82:713-21). However, this inhibitory effect was relatively modest and no conclusions were drawn about the efficacy of such treatment in reducing the overall hyperplastic response to arterial injury.

Considerable effort has been directed to preventing or reducing restenosis after vascular interventional treatment. For example, drug-eluting stents have been used to minimize coronary artery restenosis following atherectomy and balloon angioplasty. Paclitaxol and rapamycin, which inhibit cell proliferation, have been have been used for coating coronary stents. These cytostatic drugs slowly elute from the stent into the vessel wall. U.S. Pat. No. 5,283,257 describes a method for using mycophenolic acid to inhibit intimal thickening. U.S. Pat. No. 5,288,711 describes a combination of rapamycin and heparin to treat hyperproliferative vascular disease. U.S. Pat. Nos. 5,516,781 and 5,646,160 describe the administration of rapamycin alone or in combination with mycophenolic acid using a vascular stent. The problem with using antiproliferative drugs relates to their toxicity. Therapeutically effective doses of these drugs are also highly toxic when they are released into the systemic circulation. Recent case reports have also raised concerns about the long-term side effects of coated stents that elute cytotoxic drugs (McFadden et al., Lancet 2004; 364:1519-1521). Thus, it has been suggested that in certain cases the use of bare metal or non-coated stents would be preferable to toxic drug-eluting stents (Eisenberg, Lancet 2004; 364:1466-1467).

Attempts to prevent the onset, or to mitigate the effects, of intimal hyperplasia have also included, for example, systemic treatment with antiplatelet agents (e.g. aspirin, arachidonic acid, prostacyclin), antibodies to platelet-derived growth factors, and antithrombotic agents (e.g. heparin, low molecular weight heparins) (see, Ragosta et al. Circulation 1994; 89:11262-127). Clinical trials utilizing these agents, however, have shown little effect on the rate of restenosis (Schwartz, et al., N. Engl. J. Med. 1988; 318:1714-1719; Meier, Eur. Heart J. 1989; 10 (suppl G):64-68). In both angioplasty and vascular reconstructive surgery, drug infusion near the site of stenosis has been proposed as a means to inhibit restenosis. For example, U.S. Pat. No. 5,558,642 describes drug delivery devices and methods for delivering pharmacological agents to the vessel wall in conjunction with angioplasty.

Methods of providing therapeutic substances to the vascular wall by means of drug-coated stents have also been proposed. For example, methotrexate and heparin have been incorporated into a cellulose ester stent coating. The drug treated stent, however, failed to show a reduction in restenosis when implanted in porcine coronary arteries (Cox et al., Circulation 1991; 84:1171). Implanted stents have also been used to carry thrombolytic agents. For example, U.S. Pat. No. 5,163,952 discloses a thermal memoried expanding plastic stent device, which can be formulated to carry a medicinal agent by utilizing the material of the stent itself as an inert polymeric drug carrier. U.S. Pat. No. 5,092,877 discloses a stent of a polymeric material which can be employed with a coating that provides for the delivery of drugs. U.S. Pat. No. 5,837,313 discloses a method of coating an implantable open lattice metallic stent prosthesis with a drug releasing coating.

Other patents directed to devices utilizing biodegradable or biosorbable polymers include, for example, U.S. Pat. No. 4,916,193 and U.S. Pat. No. 4,994,071. U.S. Pat. No. 5,304, 121 discloses a coating applied to a stent consisting of a hydrogel polymer and a preselected drug, such as a cell growth inhibitor or heparin. Drugs have also been delivered to the interior of vascular structures by means of a polyurethane coating on a stent (U.S. Pat. No. 5,900,246).

The problem of restenosis due to subacute thrombosis and intimal hyperplasia following vascular interventional procedures remains a problem, which results in a high incidence of significant complications and even death. The present invention provides methods and devices, which address the problem of restenosis after vascular interventional procedures.

SUMMARY

Two types of restenosis can occur following an interventional procedure. One type, subacute thrombosis (SAT), results from platelet activation following procedure-related injury of the intima and/or the presence in the body of a prosthetic device (e.g., a stent or synthetic graft). Platelet activation causes blood within a vessel or prosthetic device to clot, which can lead to restenosis. This clotting almost always occurs within the fust few days following an interventional procedure. The second, more common, form of restenosis is caused by intimal hyperplasia within a vessel or prosthetic device. This new cell growth occurs over a period of several weeks or months.

According to the present invention, methods are provided for decreasing the incidence of subacute thrombosis or intimal hyperplasia by contacting an exposed vein to be used for grafting with a therapeutically effective amount of an inhibitor of a mitogen-activated protein kinase (MAPK) pathway prior to vein excision. The present invention also provides methods and devices for decreasing the incidence of SAT or intimal hyperplasia wherein a synthetic graft is contacted with a MAPK pathway inhibitor. Further, according to the present invention, the incidence of SAT or intimal hyperplasia is decreased by contacting an angioplasty balloon catheter or a stent with a MAPK pathway inhibitor. A preferred MAPK inhibitor according to the present invention is the MEK-1/2 inhibitor UO126.

Surprisingly, it was discovered that the MEK-1/2 inhibitor UO126 decreases inflammatory, myeloperoxidase-positive (MPO) cell infiltration into arterialized vein grafts but does not affect the upregulation of C reactive protein (CRP) in arterialized vein grafts. Thus, the present invention provides devices and methods for decreasing the incidence of subacute thrombosis or intimal hyperplasia wherein an exposed vein, an excised vein, a synthetic graft, a balloon angioplasty catheter or a stent is contacted with a MAPK pathway inhibitor combined with an anti-inflammatory agent.

Further, according to the present invention, methods are provided for decreasing the incidence of subacute thrombosis in a patient wherein a synthetic graft is contacted with a therapeutically effective amount of a MAPK pathway inhibitor. In one embodiment according to the present invention, the synthetic graft can be contacted by impregnating the synthetic graft with a therapeutically effective amount of a MAPK pathway inhibitor. In another embodiment, the contacting step comprises coating the synthetic graft with a therapeutically effective amount of a MAPK pathway inhibitor. According to the present invention, the contacting step can further comprise contacting the synthetic graft with an anti-inflammatory agent.

The present invention further provides methods for decreasing the incidence of subacute thrombosis in a patient whereby an angioplasty balloon catheter is contacted with a therapeutically effective amount of a MAPK pathway inhibitor. In another aspect according to the invention, a method for decreasing the incidence of subacute thrombosis in a patient is provided whereby a stent is contacted with a therapeutically effective amount of a MAPK inhibitor.

According to the present invention, methods are provided for decreasing the incidence of subacute thrombosis in a patient by contacting an excised vein to be used for grafting with a MAPK pathway inhibitor and an anti-inflammatory agent.

In accordance with the present invention, methods are provided for decreasing the incidence of intimal hyperplasia in a patient, which comprise contacting an exposed vein to be used for grafting with a therapeutically effective amount of a mitogen-activated protein kinase (MAPK) pathway inhibitor prior to vein excision. In an embodiment of the invention, methods for decreasing the incidence of intimal hyperplasia are provided wherein the contacting step comprises bathing the exposed vein to be used for grafting in a solution containing a MAPK pathway inhibitor. In another embodiment, the present invention provides methods for decreasing the incidence of intimal hyperplasia in a patient, which comprise contacting an exposed vein to be used for grafting with a therapeutically effective amount of a mitogen-activated protein kinase (MAPK) pathway inhibitor and an anti-inflammatory agent. In yet another embodiment of the present invention, methods for decreasing the incidence of intimal hyperplasia in a patient are provided which comprise contacting an excised vein to be used for grafting with a therapeutically effective amount of a MAPK pathway inhibitor and an anti-inflammatory agent.

According to the present invention, methods for decreasing the incidence of intimal hyperplasia in patient are provided comprising contacting a synthetic graft with a therapeutically effective amount of a MAPK pathway inhibitor. In one aspect according to the present invention, the incidence of intimal hyperplasia in a patient is decreased by impregnating the synthetic graft with a therapeutically effective amount of a MAPK pathway inhibitor. In another aspect, the incidence of intimal hyperplasia is decreased by coating the synthetic graft with a therapeutically effective amount of a MAPK pathway inhibitor. Further, according to the invention, methods for decreasing the incidence of intimal hyperplasia in a patient include contacting a synthetic graft with a therapeutically effective amount of a mitogen-activated protein kinase (MAPK) pathway inhibitor and an anti-inflammatory agent.

The present invention provides methods for decreasing the incidence of intimal hyperplasia in a patient which comprise contacting an angioplasty balloon catheter with an effective amount of a MAPK pathway inhibitor. In another aspect, the present invention provides methods for decreasing the incidence of intimal hyperplasia in a patient, which comprise contacting a stent with an effective amount of a MAPK pathway inhibitor.

The present invention provides a synthetic vascular graft comprising a synthetic graft and a therapeutically effective amount of a MAPK pathway inhibitor. A synthetic graft according to the invention can be impregnated with a therapeutically effective amount of a MAPK pathway inhibitor. According to the present invention, the synthetic vascular graft can be coated with a therapeutically effective amount of a MAPK pathway inhibitor. In another aspect, the synthetic vascular graft comprises a MAPK pathway inhibitor and an anti-inflammatory agent.

The present invention further provides an angioplasty balloon catheter comprising a catheter and a therapeutically effective amount of a MAPK pathway inhibitor. In one embodiment, the angioplasty balloon catheter is impregnated with an effective amount of a MAPK pathway inhibitor. In another embodiment, the angioplasty balloon catheter is coated with an effective amount of a MAPK pathway inhibitor. According to the present invention, the angioplasty balloon catheter can comprise a catheter, a MAPK pathway inhibitor and an anti-inflammatory agent.

According to the present invention, a vascular stent is provided comprising a stent and a therapeutically effective amount of a MAPK pathway inhibitor. In one embodiment, a non-metallic vascular stent is impregnated with an effective amount of a MAPK pathway inhibitor. In another embodiment, a vascular stent is coated with a therapeutically effective amount of a MAPK pathway inhibitor. In yet another embodiment, the vascular stent further comprising a stent and a therapeutically effective amount of a MAPK pathway inhibitor further comprises an anti-inflammatory agent.

The present invention provides methods for preventing subacute thrombosis in a patient, which comprise contacting a suture with a MAPK pathway inhibitor. The present invention provides methods for preventing intimal hyperplasia in a patient, which comprises contacting a suture with a MAPK pathway inhibitor.

The present invention encompasses inhibition of a MAPK pathway at any point along the pathway. For example, the invention encompasses upstream inhibition of the MAPK pathway (e.g., inhibition of MEK-1/2 with UO126) and downstream inhibition of the MAPK pathway (e.g., inhibition of ERK-1/2 production by RNAi). Thus, the invention encompasses inhibition of the activity of an enzyme along the MAPK pathway or inhibition of the production of an enzyme along the MAPK pathway.

BRIEF DESCRIPTION OF THE FIGURES

FIG. 1 illustrates the effect of pretreatment with UO126 on MAPK activation, cell proliferation, and apoptosis on excised veins in a canine model. Prior to grafting, excised autologous external jugular veins (EJV) were bathed in UO126 (80 µM) or 0.8% (v/v) DMSO (control) for 20 minutes. Autologous femoral veins were excised as a second control ("control" in the figure). Following pretreatment, each EJV was grafted to a carotid artery.

DETAILED DESCRIPTION

Figure 1A:
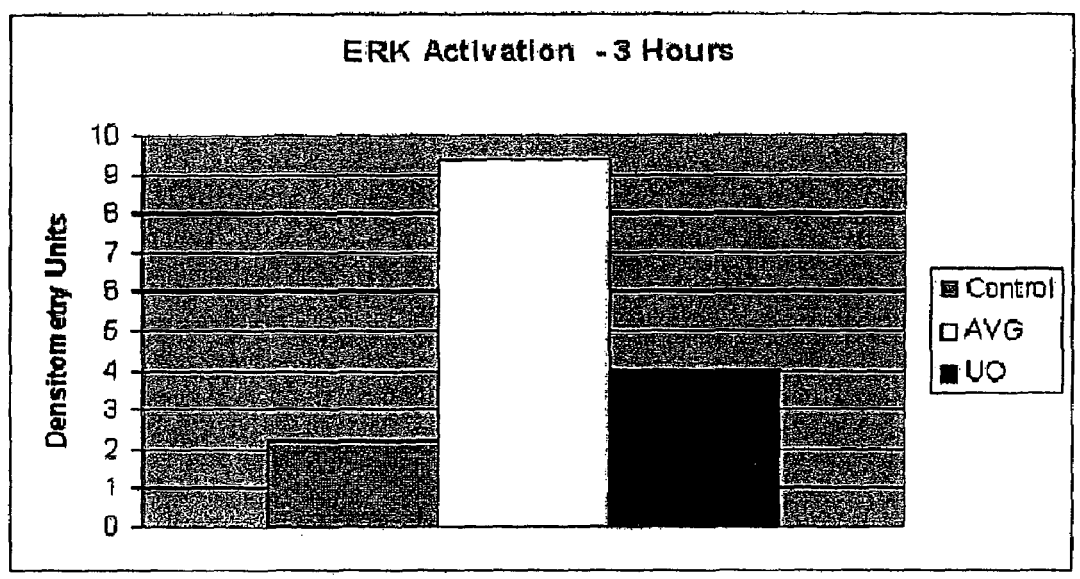
FIG. 1a shows that, at 3 hours following grafting, ERK-1/2 activation was significantly reduced in EJVs pretreated with UO126 ("UO" in the figure) relative to DMSO-treated EJVs ("AVG" in the figure). These measurements were obtained by calculating the ratio of phosphorylated (active) ERK-1/2 to total (active and inactive) ERK-1/2 by Western blotting with specific antibodies.

Following interventional treatment for arterial stenosis, blood vessels frequently restenose due to SAT and/or intimal hyperplasia. SAT occurs soon after (e.g., minutes, hours or days) following an interventional treatment, whereas intimal hyperplasia, to the point of restenosis, occurs over a longer period of time (i.e., weeks or months).

Vessel injury related to interventional treatments for atherosclerosis can occur from manipulation of the vessel to be treated (e.g., dissection, introduction of a catheter), manipulation of an autologous conduit (e.g., dissection, transection, anastomosis), and/or arterialization of a vein.

DEFINITIONS

"Arterialization" as used herein refers to injury to a vein following exposure of the vein to arterial blood pressure and arterial shear stress. Arterialization is one mechanism whereby a vein is injured. It is understood that, as used herein, methods and devices of the present invention that are applicable to veins injured by arterialization are also applicable to veins injured by other mechanisms, e.g., surgical incision of a vein.

"Contacting" or "contacted" as used herein means placing or having placed in physical proximity. For example, a vein, synthetic graft, angioplasty balloon catheter or stent can be contacted with a solution by bathing the vein, synthetic graft, angioplasty balloon catheter or stent in the solution. A synthetic graft, angioplasty balloon catheter or stent can also be contacted with a MAPK inhibitor by coating or impregnating the synthetic graft, angioplasty balloon catheter or stent with a substance, which includes a MAPK inhibitor.

"Subacute thrombosis" (SAT) as used herein refers to clotting in an artery, vein or synthetic graft that occurs within minutes, hours or days following an interventional procedure that results in, or can result in, narrowing of the lumen of the artery, vein or synthetic graft.

"Interventional treatment," "interventional procedure," or "interventional vascular procedure" as used herein means any one or more procedure for the correction or bypass of a stenotic vascular lesion. Such procedures include, for example, balloon angioplasty, stent placement and vascular bypass grafting. It is understood that the present invention also encompasses the use of stenting or vascular bypass for non-stenotic vascular conditions, e.g., vascular grafting for the treatment of an arterial aneurysm.

"Intimal hyperplasia" as used herein means a process, which includes proliferation and migration of smooth muscle cells into the intima, and deposition of extracellular matrix, leading to the narrowing of the lumen of a blood vessel. The "intima" or "endothelium" is the inner cellular monolayer lining an artery or vein. Intimal hyperplasia is the most common cause of restenosis following an interventional treatment.

"Patient" as used herein means a mammal at risk for subacute thrombosis or intimal hyperplasia or a mammal who is to undergo, or who has undergone, an interventional vascular procedure. A preferred patient is a human.

"Restenosis" as defined herein means a narrowing of the lumen of a blood vessel at a previously stenotic site (i.e., the site of balloon inflation during angioplasty), or narrowing of the lumen of a blood vessel or synthetic graft following an interventional procedure (e.g., narrowing of the venous side of an arterial-venous anastomosis following bypass surgery using a vein graft). Restenosis, as used herein, encompasses occlusion. Restenosis includes any luminal narrowing that occurs following an injury to the vessel wall. Injuries resulting in restenosis can therefore include trauma to an atherosclerotic lesion (as seen with angioplasty), a resection of a lesion (as seen with endarterectomy), an external trauma (e.g., a cross-clamping injury), or a surgical anastomosis.

"Therapeutically effective amount" as used herein means the amount of a MAPK inhibitor required to decrease the incidence of SAT or intimal hyperplasia, to delay the onset of SAT or intimal hyperplasia, or decrease the degree of obstruction caused by SAT or intimal hyperplasia.

MAPK Pathway Inhibitors

MAPK pathway inhibitors influence MAPK-mediated cellular proliferation, migration, and apoptosis involved in vascular remodeling via inhibition of at least one of the three major MAPK pathways (i.e., the ERK, JNK or p38$^{MAPK}$ pathways).

The pyridinylimidazole compound SB203580, (4-4-fluorophenyl)-2-(4-methylsulfinylphenyl)-5-(4-pyridyl) IH imidazole, (available from Calbiochem, San Diego, Calif.) is a specific inhibitor of p38$^{MAPK}$. The dosage of SB203580 typically ranges from about 10 to about 40 μmoles/L.

The flavone compound PD098059, 2-(2'-amino-3'-methoxyphenyl) oxanaphthalen-4-one, (available New England Biolabs, Inc., Beverly, Mass.) is a specific inhibitor of mammalian ERK-1/2 activation. A preferred dosage of PD098059 is about 80 μmoles/L (see Koyama et al., 1998).

UO126, 1,4-diamino-2,3-dicyano-1,4-bis[2-aminophenylthio]butadiene, (available from Cell Signaling Technology, Beverly, Mass.) is a specific inhibitor of ERK-1/2 activation. UO126 is a more potent inhibitor of ERK-1/2 activation than PD098059 (Pintucci et al., 2003). A preferred dosage of UO126 is about 40 μg/L to about 80 μmoles/L. UO126 is a preferred MAPK pathway inhibitor according to the present invention.

A solution containing a MAPK pathway inhibitor can be any one or more MAPK pathway inhibitor mixed in any sterile aqueous fluid acceptable for use during operative procedures, for example, normal saline, lactated Ringer's solution or phosphate buffered saline (PBS). UO126 is lipophilic and can be solubilized by a vehicle such as dimethyl sulfoxide (DMSO) prior to mixture in an aqueous solution. A solution containing a MAPK pathway inhibitor can optionally include an anti-inflammatory agent and/or other agents typically used in vascular interventional procedures, e.g., heparin.

Antisense Nucleic Acids and RNA Interference

According to the invention, the incidence of subacute thrombosis and/or intimal hyperplasia can be decreased as a result of inhibition of the synthesis of a MAPK. "Antisense" nucleic acid and RNA interference (RNAi) methodology can be used to prevent the synthesis of a MAPK. Thus, according to the present invention, an antisense nucleic acid or RNAi can be used to inhibit the synthesis of a MAPK and result in a decreased incidence of subacute thrombosis and/or intimal hyperplasia.

An "antisense" nucleic acid molecule or oligonucleotide is a single stranded nucleic acid molecule, which may be DNA, RNA, a DNA-RNA chimera, or a derivative thereof, which, upon hybridizing under physiological conditions with complementary bases in an RNA or DNA molecule of interest (e.g., a MAPK RNA or DNA), inhibits the expression of the corresponding gene or mRNA splice variant by inhibiting, e.g., mRNA transcription, mRNA splicing, mRNA transport, or mRNA translation or by decreasing mRNA stability. As presently used, "antisense" broadly includes RNA-RNA interactions, RNA-DNA interactions, and RNaseH mediated arrest. Antisense nucleic acid molecules can be encoded by a recombinant gene for expression in a cell (see, e.g., U.S. Pat. Nos. 5,814,500 and 5,811,234), or alternatively they can be prepared synthetically (see, e.g., U.S. Pat. No. 5,780,607).

Specific examples of synthetic antisense oligonucleotides envisioned for this invention include oligonucleotides that contain phosphorothioates, phosphotriesters, methyl phosphonates, short chain alkyl, or cycloalkyl intersugar linkages or short chain heteroatomic or heterocyclic intersugar linkages. Most preferred are those with $CH_2$—NH—O—$CH_2$, $CH_2$—$N(CH_3)$—O—$CH_2$, $CH_2$—O—$N(CH_3)$—$CH_2$, $CH_2$—$N(CH_3)$—$N(CH_3)$—$CH_2$ and O—$N(CH_3)$—$CH_2$—$CH_2$ backbones (where phosphodiester is O—$PO_2$—O—$CH_2$). U.S. Pat. No. 5,677,437 describes heteroaromatic oligonucleoside linkages. Nitrogen linkers or groups containing nitrogen can also be used to prepare oligonucleotide mimics (U.S. Pat. Nos. 5,792,844 and 5,783,682). U.S. Pat. No. 5,637,684 describes phosphoramidate and phosphorothioamidate oligomeric compounds. Also envisioned are oligonucleotides having morpholino backbone structures (U.S. Pat. No. 5,034,506). In other embodiments, such as the peptide-nucleic acid (PNA) backbone, the phosphodiester backbone of the oligonucleotide may be replaced with a polyamide backbone, the bases being bound directly or indirectly to the aza nitrogen atoms of the polyamide backbone (Nielsen et al., Science, 1991, 254:1497). Other synthetic oligonucleotides may contain substituted sugar moieties comprising one of the following at the 2' position: OH, SH, SCH$_3$, F, OCN, O(CH$_2$)$_n$NH$_2$ or O(CH$_2$)CH$_3$ where n is from 1 to about 10; C1 to C10 lower alkyl, substituted lower alkyl, alkaryl or aralkyl; Cl; Br; CN; CF$_3$; OCF$_3$; O—; S—, or N-alkyl; O—, S—, or N-alkenyl; SOCH$_3$; SO$_2$CH$_3$; ONO$_2$; NO$_2$; N$_3$; NH$_2$; heterocycloalkyl; heterocycloalkaryl; aminoalkylamino; polyalkylamino; substituted sialyl; a fluorescein moiety; an RNA cleaving group; a reporter group; an intercalator; a group for improving the pharmacokinetic properties of an oligonucleotide; or a group for improving the pharmacodynamic properties of an oligonucleotide, and other substituents having similar properties. Oligonucleotides may also have sugar mimetics such as cyclobutyls or other carbocyclics in place of the pentofuranosyl group. Nucleotide units having nucleosides other than adenosine, cytidine, guanosine, thymidine and uridine may be used, such as inosine.

The term "ribozyme" is used to refer to a catalytic RNA molecule capable of cleaving RNA substrates. Ribozyme specificity is dependent on complementary RNA-RNA interactions (for a review, see Cech and Bass, Annu. Rev. Biochem. 1986; 55: 599-629). Two types of ribozymes, hammerhead and hairpin, have been described. Each has a structurally distinct catalytic center. In a specific embodiment, the present invention contemplates the use of ribozymes designed on the basis of the RPL26 or nucleolin to induce catalytic cleavage of the corresponding mRNA, thereby inhibiting expression of the RPL26 or nucleolin. Ribozyme technology is described further in Intracellular Ribozyme Applications: Principals and Protocols, Rossi and Couture ed., Horizon Scientific Press, 1999.

The term "RNA interference" or "RNAi" refers to the ability of double stranded RNA (dsRNA) to suppress the expression of a specific gene or mRNA isoform of interest (e.g., a MAPK gene or mRNA isoform) in a homology-dependent manner. It is currently believed that RNA interference acts post-transcriptionally by targeting mRNA molecules for degradation. RNA interference commonly involves the use of dsRNAs that are greater than 500 bp; however, it can also be mediated through small interfering RNAs (siRNAs) or small hairpin RNAs (shRNAs), which can be 10 or more nucleotides in length and are typically 18 or more nucleotides in length. For reviews, see Bosner and Labouesse, Nature Cell Biol. 2000; 2: E31-E36 and Sharp and Zamore, Science 2000; 287: 2431-2433.

As used herein, the term "triplex-forming oligonucleotide" or "triple helix forming oligonucleotide" or "TFO" refers to molecules that bind in the major groove of duplex DNA and by so doing produce triplex structures. TFOs bind to the purine-rich strand of the duplex through Hoogsteen or reverse Hoogsteen hydrogen bonding. They exist in two sequence motifs, either pyrimidine or purine. According to the present invention, TFOs can be employed as an alternative to antisense oligonucleotides and can be both inhibitory and stimulatory. TFOs have also been shown to produce mutagenic events, even in the absence of tethered mutagens. TFOs can increase rates of recombination between homologous sequences in close proximity. TFOs of the present invention may be conjugated to active molecules. For review see Casey and Glazer, 2001, Prog. Nucleic Acid. Res. Mol. Biol., 67: 163-92.

Interventional Procedures

Balloon Angioplasty

Balloon angioplasty is a commonly performed percutaneous procedure. Typically, the procedure involves the insertion of a guidewire into the diseased blood vessel, which is then advanced past the region of stenosis. An angioplasty balloon catheter, which typically has an inflatable balloon attached near the distal end of the catheter, is advanced over the guidewire such that the balloon is adjacent to the stenotic lesion. After appropriate positioning, the balloon is inflated thus disrupting the arterial wall and, consequently, the stenotic region is dilated. Often, a stent is placed in the blood vessel following angioplasty to help prevent restenosis.

Contacting an Angioplasty Balloon Catheter with a MAPK Pathway Inhibitor

An angioplasty balloon catheter can be contacted with a MAPK pathway inhibitor, with or without an anti-inflammatory agent, by any means familiar to the skilled artisan, including, for example, by bathing the catheter in a solution containing a MAPK pathway inhibitor, impregnating a porous-angioplasty balloon catheter or coating an angioplasty balloon catheter (U.S. Pat. No. 6,740,678, Jorgensen, et al., Lancet 1989; 1:1106-1108; Wolinsky, et al., J. Am. Coll. Cardiol. 1990; 15:475-485; March, et al., Cardio Intervention 1992; 2:11-26; WO93/00051, WO93/00052; U.S. Pat. No. 5,304,121; Dichek, Textbook of Interventional Cardiology, Vol. 2, 61:989-1005). The injured portion of the blood vessel is, in turn, contacted by the angioplasty balloon catheter when the balloon is inflated.

A hydrophilic polymer-coated angioplasty balloon catheter is preferred in certain situations. A hydrophilic polymer-coated angioplasty balloon catheter has a hydrophilic polymer on the outer surface of the balloon which can be impregnated with a MAPK inhibitor. The hydrophilic polymer-coated angioplasty balloon catheter permits the transfer of a MAPK pathway inhibitor, with or without an anti-inflammatory agent, to the injured vessel wall upon contact between the hydrophilic polymer bearing the MAPK pathway inhibitor and the cells of the injured portion of the blood vessel. Other supports for the hydrophilic polymer are also useful, such as catheters or solid rods having a surface of hydrophilic polymer. Preferably, the catheters or rods or other substrates are flexible, to facilitate threading through the arteries to reach the point of intended application. Preferably, the hydrophilic polymer is a hydrogel polymer, a cross-linked polymer material formed from the combination of a colloid and water. Cross-linking reduces solubility and produces a jelly-like polymer that is characterized by the ability to swell and absorb liquid, e.g., liquid containing a MAPK pathway inhibitor, with or without an anti-inflammatory agent. Suitable hydrogel polymers include, for example, those selected from the group consisting of polycarboxylic acids, cellulosic polymers, gelatin, polyvinylpyrrolidone, maleic anhydride polymers, polyamides, polyvinyl alcohols, and polyethylene oxides. Preferred hydrogels are polyacrylic acid polymers available as HYDROPLUS (Mansfield Boston Scientific Corp., Watertown, Mass.), described in U.S. Pat. No. 5,091,205.

When a hydrophilic polymer-coated angioplasty balloon is used, it is not necessary to protect the balloon prior to inflation, since relatively little of the MAPK pathway inhibitor is lost in transit to the treatment site with the balloon deflated. When hydrophilic polymer-surfaced catheters or rods are used as the vehicle or substrate, the surface can be protected, e.g. by a sheath, until the point of intended application is reached, and then the protection removed to permit the hydrophilic polymer bearing the MAPK pathway inhibitor, optionally with an anti-inflammatory agent, to contact the stenotic site.

A MAPK pathway inhibitor in aqueous solution can be incorporated into the hydrophilic polymer to form a MAPK pathway inhibitor-hydrophilic polymer composition. The MAPK pathway inhibitor is incorporated without complexing or chemical reaction with the hydrophilic polymer, and is preferably relatively freely released therefrom when placed in contact with the cells at the site of injury. The resulting structure comprises a support, e.g. the balloon of the balloon catheter, on which is mounted the hydrogel, in or on which is incorporated the desired MAPK pathway inhibitor. The hydrophilic polymer is preferably adhered to the support, so that after application of the MAPK pathway inhibitor to the target cells, the hydrophilic polymer is removed with the support.

In general, when dry, the hydrophilic polymer (preferably hydrogel) coating is preferably on the order of about 1 to 10 micrometers thick, with a 2 to 5 micrometers coating typical. Very thin hydrogel coatings, e.g., of about 0.2-0.3 micrometers (dry) and much thicker hydrogel coatings, e.g., more than 10 micrometers (dry), are also possible. Typically, hydrogel coating thickness may swell by about a factor of 2 to 10 or more when the hydrogel coating is hydrated. Procedures for preparing and using a balloon with a hydrogel coating are set forth in U.S. Pat. No. 5,304,121, the contents of which are hereby incorporated by reference.

Stenting

Stents are prosthetic implants, which hold open a segment of a blood vessel. Intravascular stents are used for reducing the likelihood of vascular restenosis or closure after balloon angioplasty. Most stents currently in use are metallic and are either self-expanding or balloon-expandable. The decision to undergo a stent insertion procedure depends on certain features of the arterial stenosis. These include the size of the artery and the location of the stenosis. The function of the stent is to buttress the artery that has recently been widened using angioplasty. Stents are typically implanted via a catheter. In the case of a balloon-expandable stent, the stent is collapsed to a small diameter and slid over a balloon catheter. The catheter is then maneuvered through the patient's vasculature to the site of the lesion or the area that was recently widened. Once in position, the stent is expanded and locked in place. The stent stays in the artery permanently, holds it open, improves blood flow through the artery, and relieves symptoms.

The success of a stent can be assessed by evaluating factors such as the degree of development of thrombosis, degree of neointimal hyperplasia or smooth muscle cell migration and proliferation following stent placement, and severity of injury to the arterial wall.

Stents can be made of metal or non-metallic materials, such as polymers, or combinations thereof. Stents can be coated with a MAPK pathway inhibitor, with or without an anti-inflammatory agent, in accordance with the methods for coating an angioplasty balloon catheter as described above. Polymeric stents can be loaded with and release therapeutic agents. Methods for loading stents containing polymer are disclosed in U.S. Pat. No. 6,723,120, the contents of which are hereby incorporated by reference.

Bypass Surgery

Vascular bypass grafting is most commonly performed for the treatment of vessel stenosis. However, vascular grafts are also used for the treatment of other conditions such as arterial aneurysm or chronic renal failure (as access for hemodialysis). Vascular grafting can be performed by conventional surgery or endovascular techniques. A bypass graft can be autologous tissue, i.e., a patient's artery or vein, or synthetic, e.g., a polytetrafluoroethylene (PTFE) conduit.

Vein Graft Harvesting

Surgery for vascular bypass using an autologous vein graft includes the step of harvesting a vein segment to be used for grafting. As used herein, "vein graft" encompasses non-tubular segments of a vein, e.g., a vein "patch." Vein harvesting can be performed by open or endovascular techniques. In either technique, the vein to be harvested is first identified and then exposed (i.e., the vein is dissected free of surrounding tissue such that it can be adequately visualized). An exposed vein can be contacted with a MAPK pathway inhibitor according to the present invention by, for example, using a syringe to bathe the operative field with a MAPK pathway inhibitor solution or covering the exposed vein in a MAPK pathway inhibitor solution-soaked gauze pad. Following exposure of a sufficient length of vein for purposes of the graft, side branches of the vein are occluded (e.g., by ligation or clipping) and divided. The vein is excised by transecting its proximal and distal ends. Thus, a vein segment to be used for grafting is exposed prior to significant manipulation (e.g., transection, removal from the body) of the vein. Following excision, the harvested vein is typically kept moist, such as, for example, by immersing the harvested vein in a solution or covering the harvested vein with a moistened gauze pad. According to the invention, the solution used to moisten the harvested vein can include a MAPK pathway inhibitor, optionally with an anti-inflammatory agent, for about 20 minutes at room temperature.

Coronary Artery Bypass Graft Surgery

Coronary artery bypass grafting (CABG) is one example of vascular bypass surgery. With this procedure, a bypass graft (vein or artery) is harvested from the abdomen, chest, arm or leg and used to bypass the coronary artery distal to the site of stenosis or occlusion. When a vein graft is used, one end is anastomosed to the aorta and the other end is anastomosed to the coronary artery beyond the stenosis or occlusion. When an arterial graft is used, the proximal end is left undisturbed (thus preserving the artery's normal blood inflow) and the distal end is anastomosed to the coronary artery beyond the stenosis or occlusion.

Synthetic Grafts

Synthetic grafts are often used as conduits for non-cardiac artery bypass procedures and aneurysm surgery. Commonly used synthetic vascular grafts include expanded polytetrafluoroethylene (ePTFE) grafts (available from W. L. Gore & Associates, Inc., Flagstaff, Ariz.) and dacron (poly[ethylene terephthalate]) grafts. Synthetic grafts, in accordance with the invention, can be contacted with a MAPK pathway inhibitor by wetting the graft with a solution containing a MAPK pathway inhibitor, optionally with an anti-inflammatory agent. A synthetic graft can also be contacted with a MAPK pathway inhibitor, with or without an anti-inflammatory agent, by coating or impregnating the synthetic graft with a MAPK pathway inhibitor in accordance with the methods for coating an angioplasty balloon catheter as described above.

Anastomosis

Typically, an anastomosis (i.e., the surgical union of tubular parts) between the in situ artery or vein and the autologous or synthetic graft is created by sewing the graft to the in situ vessel with suture. Commonly used suture materials include proline (extruded polypropyline) and ePTFE, which is microporous (GORE-TEX®, available form Gore). In accordance with the present invention, the suture material to be used for the vascular anastomosis can be contacted (e.g., bathed, coated or impregnated) with a MAPK pathway inhibitor, optionally with an anti-inflammatory agent, using the techniques described above.

Anti-Inflammatory Agents

In addition to smooth cell proliferation, migration and apoptosis, inflammation is an important component of the response to injury, which can contribute to SAT or intimal hyperplasia. Markers of inflammation that have been shown to increase following vein graft arterialization in a canine model include neutrophil infiltration, thrombin activity and C-reactive protein (CRP). The increase in CRP levels is of particular significance because high circulating levels of this protein are an independent predictor of cardiovascular disease (Blake and Ridker, J Am Coll Cardiol. 2003; 41:S37-S42; Yeh and Willerson, Circulation. 2003; 107:370-372).

Anti-inflammatory agents according to the present invention include synthetic thrombin inhibitors (e.g., hirudin, ximegalatran and argatoban); serine protease inhibitors (e.g., aprotinin); non-steroidal anti-inflammatory agents; COX-2 inhibitors; and glucocorticoids. Non-steroidal anti-inflammatory agents include, for example, aspirin, diclofenac, indomethacin, sulindac, ketoprofen, flurbiprofen, ibuprofen, naproxen, piroxicam, tenoxicam, tolmetin, ketorolac, oxaprosin, mefenamic acid, fenoprofen, nambumetone, acetaminophen, and mixtures thereof. COX-2 inhibitors include, for example, nimesulide, NS-398, flosulid, L-745337, celecoxib, rofecoxib, SC-57666, DuP-697, parecoxib sodium, JTE-522, valdecoxib, SC-58125, etoricoxib, RS-57067, L-748780, L-761066, APHS, etodolac, meloxicam, S-2474, and mixtures thereof. Glucocorticoids include, for example, hydrocortisone, cortisone, prednisone, prednisolone, methylprednisolone, meprednisone, triamcinolone, paramethasone, fluprednisolone, betamethasone, dexamethasone, fludrocortisone, desoxycorticosterone, and mixtures thereof.

EXAMPLES

The present invention is also described by means of the following examples. However, the use of these or other examples anywhere in the specification is illustrative only and in no way limits the scope and meaning of the invention or of any exemplified term. Likewise, the invention is not limited to any particular preferred embodiments described herein. Indeed, many modifications and variations of the invention may be apparent to those skilled in the art upon reading this specification and can be made without departing from its spirit and scope.

Example 1

Arterialization Produces Vessel Injury and Leads to Intimal Hyperplasia

Carotid artery bypass using reversed autologous external jugular vein (EJV) was performed on 29 purpose-bred mongrel dogs. Following skin incision, the EJV was exposed with a "no-touch" technique, and the side branches were clipped and divided. The dogs received heparin systemically (100 U/kg) and the ipsilateral common carotid artery was dissected free of the surrounding tissue. The EJV was ligated and excised. The lumen of the EJV was flushed with plasmalyte solution without distending the vein. A segment of the excised vein was removed and labeled ("control 1"). The EJV was reversed and grafted to the common carotid artery in an end-to-side fashion with 7-0 polypropylene suture, and the carotid artery was ligated and divided. See Saunders et al., J Thorac Cardiovasc Surg. 2004; 127:1276-1284.

As additional controls, three dogs underwent EJV to EJV vein-to-vein bypass and 2 dogs underwent carotid artery to carotid artery artery-to-artery bypass. Harvested femoral vein and artery were used as controls for the MAPK activation assays.

The vein grafts were harvested at the following times post-operation: 30 minutes; 3, 8 and 24 hours; and 4, 7, 14 and 28 days. As a control at the time of harvesting, a segment of the contralateral EJV was excised ("control 2"). An arteriotomy was made in the carotid artery distal to the vein graft to confirm the patency of the graft. The vein graft was excised and a 5-mm segment from its midpoint was fixed in formaldehyde for subsequent histologic examination.

Sample Processing

All vein grafts were patent at the time of harvesting. Vein samples were harvested and processed as previously described (Bizekis et al., J Thorac Cardiovasc Surg 2003; 125:659-665). A segment of each sample was removed and fixed in 3.7% formaldehyde for hematoxylin and eosin staining and immunohistochemical analysis.

Western Blotting

Equal amounts of vein extract protein (20-60 μg) were electrophoresed in sodium dodecyl sulfate/10% polyacrylamide gels and blotted onto PVDF membranes (Millipore, Bedford, Mass.). The membranes were incubated with antibodies to the active (phosphorylated) forms of either ERK-1/2 or p38$^{MAPK}$ (Cell Signaling Technology, Beverly, Mass.). As a control for equal loading and transfer, the membranes were stripped and reprobed with antibodies to the total (i.e., phosphorylated plus non-phosphorylated) forms of the corresponding signal protein (anti-ERK-2, anti-p38$^{MAPK}$ antibodies, respectively) (available from Santa Cruz Biotechnology, Inc., Santa Cruz, Calif.).

Activation of the JNK pathway was assessed using a pull-down assay that detects phosphorylation of a GST-Jun fusion protein using c-Jun as both the bait and the substrate for JNK (Cell Signaling Technology). As a control for equal loading and transfer, the membranes were stripped and reprobed with anti-total c-Jun antibody (Cell Signaling Technology). The membranes were incubated with horseradish peroxidase-labeled anti-rabbit immunoglobulin G antibodies (Amersham Pharmacia Biotech, Inc., Piscataway, N.J.) and antigen-antibody complexes were detected by enhanced chemiluminescence (Lumilight, Roche, Indianapolis, Ind.).

Quantitative analysis of the immunoreactive bands was performed by scanning densitometry with Kodak 1D Image Analysis software (Kodak, Rochester, N.Y.). The active forms of each protein were normalized to the total amount of the corresponding protein, and kinase activity was measured in arterialized vein grafts compared with contralateral EJVs.

Histologic and Immunohistochemical Analysis

Cross sections (4-6 μm) of fixed vein segments were stained with hematoxylin and eosin for morphologic examination or Van Gieson stain to visualize the elastic fibers. For immunodetection of active MAPKs, paraffin-embedded sections were processed with the ABC staining kit (Santa Cruz Biotechnology, Inc.) using the anti-active MAPK antibodies described above, except that phospho-p38$^{MAPK}$ monoclonal antibody (Cell Signaling Technology) was used. Sections were also immunostained for α-smooth muscle cell actin (α-SMA), a smooth muscle cell marker, using a specific monoclonal antibody (Sigma, St. Louis, Mo.).

Cell Proliferation and Apoptosis

Cell proliferation was monitored by Western Blot analysis of proliferating cell nuclear antigen (PCNA) expression in vein graft extracts using monoclonal antibodies to PCNA (LabVision, Fremont, Calif.). Lysates of proliferating endothelial cells were used as a positive control for PCNA expression. Detection of antigen-antibody complexes and scanning densitometry were performed as described above. For immunohistochemical detection of PCNA, paraffin-embedded sections of the vein samples were analyzed with the same antibodies used for Western blotting.

Apoptotic cells were detected by staining cross sections (4-6 μm) of paraffin-embedded vein segments for ladderized DNA using the terminal deoxynucleotidyl transferase-mediated 2'-deoxyuridine 5'-triphosphate nick end labeling (TUNEL) assay (Oncogene Research Products, Boston, Mass.). The sections were counterstained with nuclear stain Hoechst 33342 and analyzed with a fluorescence microscope (Zeiss Axioskop 2, Carl Zeiss, Inc., Thornwood, N.Y.).

Results

Vein Graft Arterialization Produces Vascular Injury, Remodeling and Intimal Hyperplasia EJV graft bypass of the carotid artery produced the following histologic changes in the vein graft: (1) early signs of endothelial sloughing, leukocyte lining of the luminal surface, and leukocyte invasion of the vein wall; (2) at 1 to 4 days post-operation, the vein grafts dilated and became edematous with occasional hemorrhage in the media; (3) at 1 week, small areas of intimal hyperplasia were observed; and (4) at 28 days, the areas of intimal hyperplasia evolved into eccentric lesions that encroached into the vein graft lumen.

ERK and $p38^{MARK}$ Pathways are Activated in a Multimodal Manner Following Vein Graft Arterialization Arterialization of the EJV grafts resulted in ERK-1/2 activations at 30 minutes and 3 hours after anastomosis. An additional, but not statistically significant, activation of ERK-1/2 occurred at 4 days post-anastomosis. Arterialization of the EJV grafts resulted in statistically significant $p38^{MARK}$ activations at 30 minutes, 3 hours, and 4 days post-anastomosis. In contrast with data reported for arterial balloon injury, EJV graft arterialization did not result in consistent JNK activation. Confirming the Western blot results, immunohistochemical analysis of the arterialized vein grafts showed active ERK-1/2 and $p38^{MAPK}$ (associated with α-smooth muscle actin (SMA) positive cells at 30 minutes, 3 hours, and 4 days.

Vein Graft Arterialization Induces Medial Cell Proliferation and Apoptosis

PCNA expression was not induced at 30 minutes, 3 hours, or 8 hours. A modest induction of PCNA expression was observed at 24 hours in the vein grafts compared to controls. From 4 days to 28 days, about an 8- to 14-fold increase of PCNA expression was detected in the grafted veins over control, and these findings were confirmed by immunohistochemical analysis showing strong staining for PCNA in the inner media and neointima.

TUNEL assay of sections of the arterialized vein grafts and contralateral EJVs showed increased apoptosis in the inner media of the arterialized EJVs at 8 hours and 24 hours after arterialization. Apoptosis was barely detected at later time points. These data indicate that early apoptosis is accompanied by, and followed by, cellular proliferation.

Example 2

UO126 Reduces ERK Activation, Suppresses Smooth Muscle Cell Proliferation, and Increases Smooth Muscle Cell Apoptosis in Arterialized Vein Grafts The canine model described in Example 1 above was used for these experiments. Prior to grafting, the excised autologous EJVs were fully immersed for 20 minutes at room temperature in about 5 ml of a solution containing 80 μmmoles/L of UO126 (solubilized with DMSO and diluted in PBS) or vehicle (DMSO, 0.8%) alone in PBS. Each EJV was grafted to a carotid artery. Autologous femoral vein was excised but not treated or grafted. The veins were sampled and assayed as described in Example 1.

MAPK inhibition was evaluated by Western blot analysis, at 3 hours post-grafting, the time at which MAPK activation has been shown to be maximal (Saunders, et al., J Thorac Cardiovasc Surg. May 2004; 127(5):1276-1284). See FIG. 1a. Three hours following grafting, ERK-1/2 activation was significantly reduced in EJVs pretreated with UO126 relative to DMSO-pretreated EJVs. These measurements were obtained by calculating the ratio of phosphorylated (active) ERK-1/2 to total (active and inactive) ERK-1/2 by Western blotting with specific antibodies.

Figure 1B:
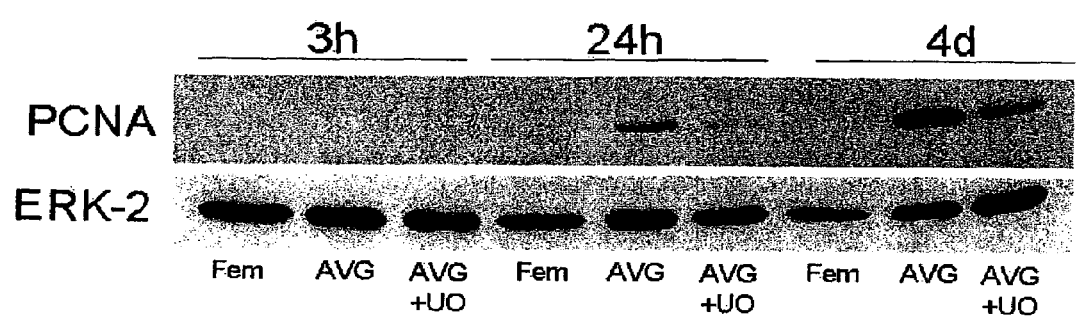
FIG. 1b shows a Western blot analysis of the three vein groups. At 24 hours and 4 days post-grafting, PCNA expression was markedly decreased in the UO126-pretreated EJVs relative to the DMSO-pretreated EJVs (upper panel). ERK-2 expression was analyzed as a control for equal loading and transfer (lower panel).

PCNA expression was measured at 1 day and 4 days post-anastomosis by Western blot analysis of the three vein groups. See FIG. 1b. At 24 hours and 4 days post-grafting, PCNA expression was markedly decreased in the UO126-pretreated EJVs relative to the DMSO-pretreated EJVs (upper panel). ERK-2 expression was analyzed as a control for equal loading and transfer (lower panel).

TUNEL assays of control femoral vein, DMSO-pretreated EJV and UO126-treated EJV were performed at 1 day and 4 days post-anastomosis. UO126 pretreated veins had a marked and sustained (up to 4 days) induction of medial cell apoptosis following UO126 pretreatment of the grafted vein.

Thus, UO126 pretreatment, compared to DMSO-pretreatment, resulted in (1) a significant decrease of MAPK activation 3 hours following vein graft arterialization; (2) a marked decrease in cellular proliferation (as measured by PCNA expression) at 1 day and 4 days post-arterialization; and (3) a marked and sustained increase of medial cell apoptosis (as measured by TUNEL assay). These experiments suggest that pretreatment of a vein graft with the MAPK inhibitor UO126 reduces intimal hyperplasia following vessel injury.

Example 3

Pre-Treatment with UO126 Decreased Arterialized Vein Graft Infiltration by MPO Cells and Did not Affect CRP Upregulation Inflammation is a key component of a vessel's response to injury. Using the canine model described in Example 1, postoperatively high levels of C reactive protein (CRP) and infiltration by inflammatory myeloperoxidase-positive (MPO) cells were found in association with the arterialized vein grafts. The MPO cells were mostly polymorphonuclear neutrophils (PMN). In light of these findings, experiments were performed to investigate the potential affect of ERK-1/2 pathway inhibition on the inflammatory response in arterialized vein grafts.

Figure 2:
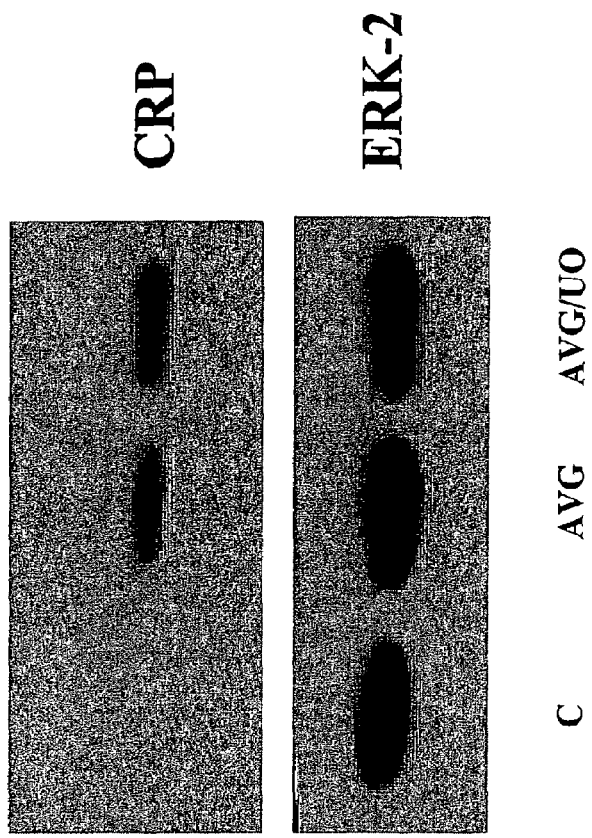
FIG. 2 shows the results of Western blot analysis of vein graft protein with anti-CRP antibody (upper panel) or anti-ERK-2 antibody as a loading control (lower panel) in contralateral (ungrafted) vein ("C"), arterialized vein graft ("AVG") and arterialized vein graft pre-treated with 80 µM UO126 ("AVG/UO").
Figure 3:
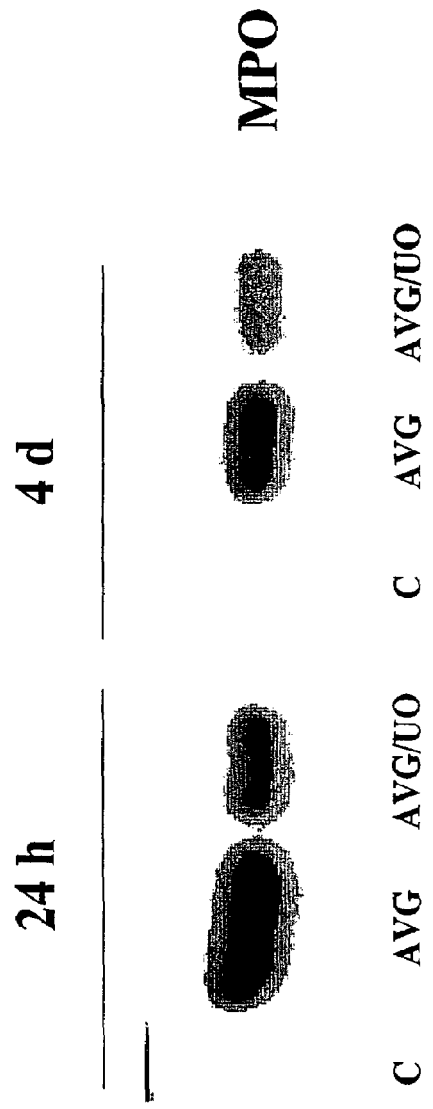
FIG. 3 shows the results of Western blot analysis of vein graft protein with anti-myeloperoxidase (MPO) antibody in contralateral (ungrafted) vein ("C"), arterialized vein graft ("AVG") and arterialized vein graft pre-treated with 80 µM UO126 ("AVG/UO").

This experiment, which also used the canine model described in Example 1, investigated the levels of CRP and MPO cells in arterialized vein grafts immersed in a solution of UO126 (80 μM/L) (solubilized with DMSO and diluted in PBS) prior to grafting (i.e., pretreated grafts), arterialized vein grafts that were not pretreated, and contralateral ungrafted, un-pretreated external jugular veins. Western blot analysis of the veins with anti-CRP antibody or ERK-2 antibody (as a loading control) 24 hours post-operatively showed that pretreatment with UO126 does not affect the upregulation of CRP in arterialized vein grafts. See FIG. 2. However, as demonstrated by Western blotting using anti-MPO antibody, pretreatment with UO126 significantly downregulated the levels of MPO cells associated with arterialized vein grafts when measured 24 hours and 4 days post-operatively. See FIG. 3.

Therefore, in addition to decreasing cell proliferation and increasing apoptosis, UO126 was shown in this experiment to reduce arterialized vein graft infiltration by MPO cells. However, the increase of CRP in arterialized vein grafts appears to be independent of ERK-1/2 activation. These experiments suggest that the MAPK inhibitor UO126 reduces inflammation and, therefore, SAT. These experiments also suggest the use of a MAPK inhibitor in combination with an anti-inflammatory agent such that the inflammatory response, including the increase in CRP, in arterialized vein grafts is reduced.

Example 4

UO126 Reduces Vein Wall Thickness (Intima+Media) to Luminal Circumference Ratio in Arterialized Vein Grafts The experimental procedure followed in the canine model described in Examples 1, 2, and 3 was applied to white New Zealand rabbits fed a 1% cholesterol chow. Prior to grafting, the excised autologous EJVs were fully immersed for 20 minutes at room temperature in about 5 ml of a solution containing 80 μmoles/L of UO126 (solubilized with DMSO and diluted in PBS) or vehicle (DMSO, 0.8%) alone in PBS. Each EJV was grafted to a carotid artery. Autologous femoral vein was excised but not treated or grafted. The veins were fixed in formaldehyde, and sections stained with hematoxylin/eosin were used for the following analysis.

Vein wall thickness (intima+media) to luminal circumference ratio was measured in AVG harvested at 28 days from cholesterol-fed rabbits (ratio mean value+/−SD):
DMSO controls=358.2+/−190.3
UO126 treated=288.8+/−109.5

Because the distribution of these ratios varied significantly from normal by both the Kolmogorov-Smirnov and Shapiro-Wilk tests of normality, nonparametric statistics were used to test the significance of the difference in ratios between experimental groups. The two-sample Kolmogorov-Smirnov test showed the difference to be significant at $p=0.012$.

These experiments suggest that early treatment of a vein graft with UO126 results in a long-term (28 days) reduction of the vein wall thickness to luminal circumference ratio.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all values are approximate, and are provided for description.

Patents, patent applications, publications, product descriptions, and protocols are cited throughout this application, the disclosures of which are incorporated herein by reference in their entireties for all purposes.

The invention claimed is:

1. A method for reducing intimal hyperplasia in a diseased or injured artery of a patient, which method comprises: (a) contacting a vascular stent for about 20 minutes with a solution comprising a therapeutically effective amount of an ERK1/2 pathway inhibitor prior to stent implantation into the artery, and (b) implanting said vascular stent into the diseased or injured artery of the patient so that the artery is exposed to the therapeutically effective amount of the ERK1/2 pathway inhibitor, wherein said exposure provides long-term inhibition of intimal hyperplasia in the artery, and wherein the ERK1/2 pathway inhibitor is UO126.

2. The method of claim 1, which further comprises contacting the artery with an anti-inflammatory agent.

* * * * *